United States Patent [19]

Shirato et al.

[11] Patent Number: 4,652,364

[45] Date of Patent: Mar. 24, 1987

[54] APPARATUS FOR ADJUSTING THE CONCENTRATION OF A SOLUTION

[75] Inventors: Kozo Shirato, Saitama; Kazuo Hiraizumi, Chiba; Masashi Kobayashi, Tokyo; Kazuyasu Kawashima, Kanagawa, all of Japan

[73] Assignee: Erma Inc., Tokyo, Japan

[21] Appl. No.: 816,107

[22] Filed: Jan. 3, 1986

[30] Foreign Application Priority Data

Apr. 5, 1985 [JP] Japan .............................. 60-51599[U]

[51] Int. Cl.⁴ .............................................. B01D 13/00
[52] U.S. Cl. ...................................... 210/87; 210/188; 210/321.2
[58] Field of Search ................... 210/188, 321.1, 321.2, 210/321.3, 321.4, 87

[56] References Cited

U.S. PATENT DOCUMENTS 3,475,331 10/1969 McLain ............................ 210/321.1
3,598,727 8/1971 Willock ........................... 210/188 X Primary Examiner—Frank Spear
Attorney, Agent, or Firm—Watson, Cole, Grindle & Watson

[57] ABSTRACT

An apparatus for adjusting concentration of a solution comprises a plurality of semipermeable membrane tubes located within a container, a liquid A supply pipe connected to the container and communicating with the interior of said semipermeable membrane tubes and a liquid B supply pipe connected to said container to communicate with the exterior of the tubes.

1 Claim, 1 Drawing Figure

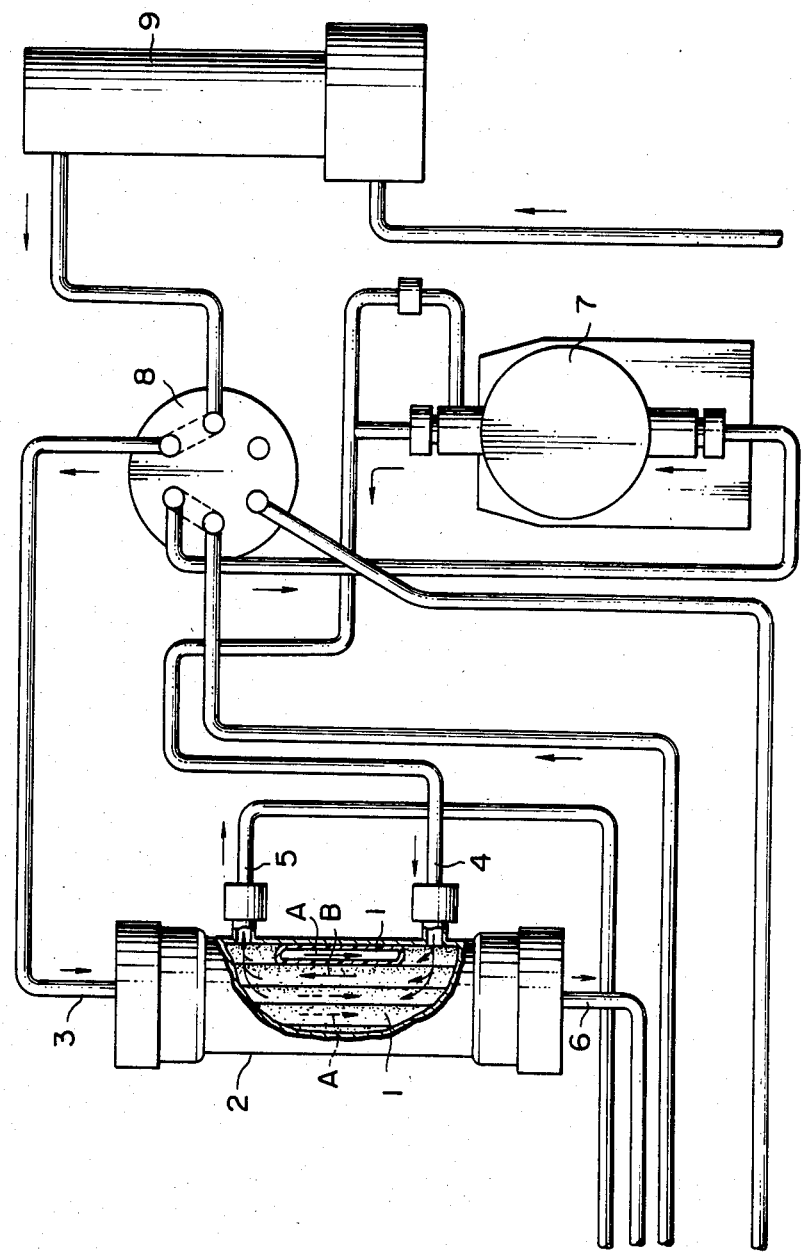

APPARATUS FOR ADJUSTING THE CONCENTRATION OF A SOLUTION

The present invention relates generally to apparatus for adjusting the concentration of a solution and, more particularly, to such an apparatus which can provide such an adjustment continuously.

BACKGROUND OF THE INVENTION

In the conventional adjustment of the concentration of solution, an amount of solvent such as, for example, water (liquid A) and an amount of dissolution liquid such as, for example, a solution of salt (liquid B) whose concentration is to be adjusted are measured and mixed under a batch type processing to yield a combined solution (liquid A+liquid B) having the desired concentration. However, when batch type processing for adjustment of solution concentration used in, for example, a gradient process in a liquid chromatography (a process in which composition (concentration) of eluate flowing in a column is gradually varied and flowed), some disadvantages appear in that a change-over valve for solvent and dissolution liquid had to be operated and they had to be agitated. As a result, the process took a long time, bubbles were mixed in the liquid during agitation and an analysis with high accuracy could not be performed.

SUMMARY OF THE INVENTION

The present invention eliminates the above-noted disadvantages and provides an apparatus for adjusting concentration of solution in which solution with desired concentration can be taken continuously in an on-line system.

The present apparatus for adjusting the concentration of a solution to accomplish the above-mentioned purposes comprises a plurality of semipermeable membrane tubes located within a container, a liquid A supply pipe connected to the container and communicating with the interior of said semipermeable membrane tubes and a liquid B supply pipe connected to said container to communicate with the exterior of the tubes.

When liquid A (for example, a solvent such as water) flows within the semipermeable membrane tubes and liquid B (for example, dissolution such as a 20% salt solution) flows outside the semipermeable membrane tubes but within the container, the semipermeable membrane tubes allow semipermeation with the result that the liquids A and B are permeated, diffused and mixed with each other under a principle of dialysis and they flow from the semipermeable membrane tubes as solution with a desired concentration (for example, a salt solution of 15%).

BRIEF DESCRIPTION OF THE DRAWINGS

The sole FIGURE is a schematic illustration, partially in section, of a preferred apparatus according to the invention.

DETAILED DESCRIPTION OF THE PREFERRED EMBODIMENTS

Referring now to the drawing, the illustrated apparatus according to the invention comprises container 2 containing a plurality of semipermeable membrane tubes 1 adapted to carry liquid A. Tubes 1 are fine longitudinally hollow tubes with an outer diameter of, for example, one to several millimeters, an inner diameter of 0.5 to several millimeters and a length of about 250 mm. Tubes 1 are of a material having dialysis characteristics such as a fibrous film of polyvinyl alcohol or a porous film of tetrafluoroethylene. A plurality of semipermeable membrane tubes 1, e.g., several hundreds to several thousands, are stored and arranged in container 2.

Container 2 protects the semipermeable membrane tubes 1 and also contains liquid B flowing therethrough. Container 2 is formed of a generally cylindrical shape and may be formed of metal material or resin material such as acrylic resin. Liquid A supply pipe 3 is connected to communicate with an inlet of each of the semipermeable membrane tubes 1 at the top of container 2 and a waste liquid discharging pipe 5 is connected to communicate with the interior of the container. A solution injection pipe 6 is connected to communicate with an outlet of each of semipermeable membrane tubes 1 below container 2, and liquid B supplying pipe 4 is connected to communicate with the interior of the container. That is, liquid A supply pipe 3 and the liquid B supply pipe 4 are arranged such that liquids A and B flow countercurrently to each other in the container 2 and are separated by semipermeable membrane tubes 1. This arrangement of liquid A supply pipe 3 and liquid B supply pipe 4 enables solution with the desired concentration to be efficiently made in a short period of time. That is, even if the number of semipermeable membrane tubes 1 are reduced and their length shortened, a solution with a desired concentration can be attained in a short period of time and also the flow rate of the solution can be reduced.

Liquid A may be a solvent such as water and liquid B may be a dissolution such as a solution of water with high concentration or alcohol, etc. Alternatively, liquid A may be a dissolution and the liquid B may be a solvent. That is, in the present device, in principle, as long as any liquid is flowing in the liquid A supply pipe 3 and liquid B supply pipe 4, a solution with a desired concentration can be attained. However, since accumulation of liquid in the container 2 may be possible, the solution to be discharged from waste liquid discharging pipe 5 of container 2 may have a dispersion in concentration. Consequently, a liquid acting as a reference liquid preferably flows in liquid A supply pipe 3 and the solution flows in the liquid B supply pipe 4.

It is also preferable that container 2 be arranged vertically to cause liquid A to flow from top to bottom and liquid B to flow from bottom to top. That is, since liquid A and the liquid B are permeated and dispersed with each other in each of semipermeable membrane tubes 1 being held, when the reference liquid flows in liquid A supply pipe 3 and the solution flows in liquid B supply pipe 4, a concentration gradient is produced in container 2 through which liquid B flows. As a result of the vertical arrangement of container 2 and a flow of liquid A from top to bottom as well as a flow of liquid B from bottom to top, liquid A is caused to flow from a point having a low concentration of solution (liquid B) toward a point having a high concentration of solution, its concentration is gradually increased and the liquid may flow out of the outlets of semipermeable membrane tubes 1 as solution with the desired concentration. Experiments have shown that with a horizontal orientation of container 2, a flow of liquid A from bottom to top or a flow of liquid B from top to bottom and a flow of both liquids A and B in the same direction, the concentration of the solution produced is not stable and a solution with a desired concentration and high accuracy may not be produced.

When liquid A flows from liquid A supply pipe 3 into each of semipermeable membrane tubes 1 and the liquid B flows from liquid B supply pipe 4 into container 2, each of the semipermeable membrane tubes acts as a semipermeable membrane, the liquids A and B are permeated and dispersed to each other under a principle of dialysis, a solution with a desired concentration is discharged from the outlets of the semipermeable membrane tubes and the waste liquid is discharged from waste liquid discharging pipe 5 of the container. At this time, adjustment of the flow rate of liquid B under a constant flow rate of liquid A enables solution with any desired concentration to be produced under a specified flow rate.

Other components which may be included in the apparatus are liquid feeding pump 7 for supplying liquid B into container 2, deaerator 8 for deaerating gas contained in solution in the liquids A and B, and flow meter 9 for measuring the flow rate of liquid A. Deaerator 8 is effective for obtaining an analytical value with less noise and with a high accuracy in case that the liquids A and B are deaerated in advance and the produced solution with a desired concentration is supplied as for use in liquid chromatography. Deaerator 8 at the same time prevents bubbles from being generated, particularly in liquid B, which could stay in container 2 due to a difference in temperature of the surrounding atmosphere.

Since the present apparatus for adjusting concentration of solution is constructed as described above, it is possible to obtain a solution of desired concentration continuously in an on-line system. In addition, it is possible to provide a simple and less expensive structure.

It is claimed:

1. An apparatus for adjusting concentration of a solution, the apparatus comprising a container, a plurality of semipermeable membrane tubes located with the container and oriented vertically, a liquid A supply pipe connected to the container and communicating with the interior of said semipermeable membrane tubes, a liquid B supply pipe connected to said container to communicate with the exterior of the tubes, a solution injection pipe communicating with the interior of the tubes and a waste liquid discharge pipe communicating with the exterior of the tubes, a deaerator in the liquid B supply pipe, a deaerator in the liquid A supply pipe, a pump for supplying liquid B in liquid B supply pipe and a flow meter for measuring flow of liquid A in liquid A supply pipe.

* * * * *